United States Patent [19]

Garland et al.

[11] 4,012,516
[45] Mar. 15, 1977

[54] PHARMACOLOGICALLY ACTIVE COMPOSITIONS

[75] Inventors: Lawrence George Garland, Biggin Hill; Michael John Follenfant, Croydon; James Edward Tateson, Orpington, all of England

[73] Assignee: Burroughs Wellcome Co., Raleigh, N.C.

[22] Filed: Jan. 23, 1976

[21] Appl. No.: 651,903

[30] Foreign Application Priority Data

Jan. 24, 1975 United Kingdom ............... 3140/75

[52] U.S. Cl. ............................... 424/269; 424/275; 424/276

[51] Int. Cl.$^2$ ................ A61K 31/38; A61K 31/39; A61K 31/41

[58] Field of Search ................... 424/275, 276, 269

[56] References Cited

UNITED STATES PATENTS 3,905,989  9/1975  Hodson et al. ..................... 424/269

Primary Examiner—Stanley J. Friedman
Attorney, Agent, or Firm—Donald Brown

[57] ABSTRACT

A synergistic combination comprising
 a. a tricyclic compound having anti-allergic activity and
 b. a compound having $\beta_2$ adrenergic stimulant activity useful for the treatment or prophylaxis of allergic conditions. Also provided is the use of such combinations in human and veterinary medicine.

13 Claims, No Drawings

PHARMACOLOGICALLY ACTIVE COMPOSITIONS

The present invention relates to a combination of substances useful in the treatment or prophylaxis of allergic conditions; to the treatment of such conditions; and to pharmaceutical compositions of the combinations.

It has been found that the anti-allergic effect of 3-(5-tetrazolyl)thioxanthone-10,10-dioxide and certain other orally active anti-allergic compounds and their salts (hereinafter referred to as the "compounds of formula (I)") are potentiated by bronchodilators acting directly or indirectly by stimulation of $\beta_2$-adrenoceptors (hereinafter referred to as the "stimulants").

The anti-allergic activity of the combinations of the present invention has been demonstrated by measurement of histamine release from human chopped lung tissue passively sensitized in vitro with reaginic antibody when challenged with the homologous antigen (Br.Med. J. 3,272 (1968)). The release of histamine from lung preparations treated in this way is known to be inhibited by both the stimulants and the compounds of formula (I) when used separately, but it has now been shown that their combined effect is greater than was to be expected from a knowledge of the activity of the individual components, and in particular the inhibition is greater than the sum of the individual responses when the components are used separately at the same concentrations. The compounds of formula (I) are represented by the formula

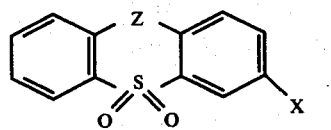
(I)

wherein Z is carbonyl (C=O) or oxygen (—O—), and X is carboxy or a 5-tetrazolyl group, and salts thereof with pharmaceutically acceptable cations. Of especial value are:

3-(5-tetrazolyl)thioxanthone-10,10-dioxide (II);

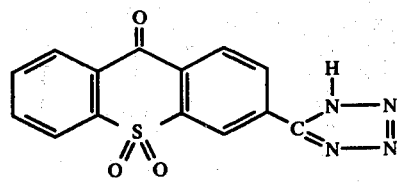
(II)

3-carboxythioxanthone-10,10-dioxide (III);

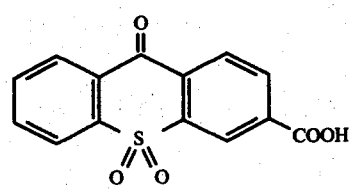
(III)

and 2-(5-tetrazolyl)phenoxathiin-10,10-dioxide (IV)

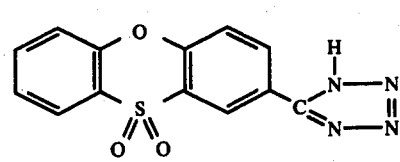
(IV)

and their salts. The compounds of formula (I) may be synthesised by any method known in the art, in particular by the methods described in Belgium patent specification No. 799,776.

Stimulants which may be used to potentiate the anti-allergic activity of the compounds of formula (I) are:
Salbutamol ($\alpha'$-t-butylaminomethyl-4-hydroxy-m-xylene-$\alpha',\alpha^3$-diol) and salts thereof;
Terbutaline (1-(3,5-dihydroxyphenyl)-2-(t-butylamino)ethanol) and salts thereof;
Orciprenaline ((+)-1-(3,5-dihydroxyphenyl)-2-isopropylamine ethanol) and salts thereof;
Isoetharine ($\alpha$-(1-isopropylaminopropyl)protocatechuyl alcohol) and salts thereof;
Fenoterol (1-(3,5-dihydroxyphenyl)-2-[(1-(4-hydroxybenzyl) ethyl)amino]ethanol) and salts thereof;
Trimetoquinol (1-(3,4,5-trimethoxybenzyl)-6,7-dihydroxy isoquinoline) and salts thereof;
Carbuterol ([5-[2-(t-butylamino)-1-hydroxyethyl]-2-hydroxy phenyl]urea) and salts thereof.

While an anti-allergic compound of formula (I) and a stimulant may be administered separately but concurrently for the treatment of allergic conditions, they are conveniently administered together as a combination of a compound of formula (I) and a stimulant or a salt thereof. For use in medical practice such a combination is conveniently presented for treatment or prophylaxis as an orally ingestible pharmaceutical composition comprising the active ingredient combination together with a pharmaceutically acceptable carrier. Advantageously the compositions take the form of discrete units, such as tablets, capsules or cachets each containing a predetermined amount of the combination of active ingredients. The combination may also be presented as a powder or granules, to be administered either alone or in a solution or suspension in a liquid medium for oral administration. Preferred pharmaceutical compositions contain from 5 to 95% by weight of the combination of active ingredients.

The compositions may be made by any method known in the art of pharmacy, which includes tabletting by compression or moulding, granulating, grinding, stirring, coating, milling and tumbling. One or more carriers may be included in a composition of this invention and these include diluents, solutes, buffers, flavouring, binding, dispersing, surface active, thickening, lubricating, and coating materials, preservatives, antioxidants and bacteriostats, and any other pharmaceutically acceptable excipients.

The combination of a stimulant and a compound of formula (I) is administered for the treatment or prophylaxis of allergic conditions at doses of the substances which together produce an anti-allergic effect.

In general, the substances are administered in the range of the ratios of 1 part of stimulant to 1 part by weight of a compound of formula (I) and 1 part of stimulant to 200 parts by weight of a compound of formula (I). A suitable unit dose for a human is from 5 to 100% by weight of the known bronchodilator dose of a stimulant for humans and from 1 to 400 mg of a compound of formula (I), expressed as weights of the appropriate acid (or base as appropriate). Thus in the case of the stimulant being salbutamol, the dose is from 1 to 20 mg of the compound. Such unit doses may be repeated three times a day.

Preferred doses will vary depending on the choice of the anti-allergic compound of formula (I) and the stimulant, and on the nature and severity of the allergic condition to be treated. Such conditions include asthma and other allergic chest conditions, hay fever (allergic rhinitis), conjunctivitis, urticaria and eczema. In particular they are of value in reaginic mediated Type I hypersensitivity asthma ('extrinsic asthma') and the so-called 'intrinsic asthma' in which no sensitivity to extrinsic antigen can be shown.

Any novel feature of the present invention may be claimed, principally but not exclusively, including the following features:

a. A pharmaceutical preparation suitable for use in treatment of asthma comprising a compound of formula (I) and an orally active stimulant; in association with a pharmaceutically acceptable carrier therefor.

b. A method for the treatment or prophylaxis of an allergic condition in a mammal comprising the concurrent or sequential administration to the mammal of an anti-allergic non-toxic amount of an orally active stimulant and a compound of formula I.

c. A method for the preparation of a pharmaceutical composition suitable for use in the treatment or prophylaxis of an allergic condition comprising the admixture of a compound of formula I and an orally active stimulant, together with a pharmaceutically acceptable carrier therefor.

d. The combination of a compound of formula I and an orally active stimulant.

e. The combination of Salbutamol and a compound of formula II or a salt thereof.

The following Examples are given to illustrate, but in no way limiting, the present invention.

Example 1

| Tablet | |
| --- | --- |
| 3-(5-Tetrazolyl)thioxanthone-10,10-dioxide | 100 mg |
| Salbutamol | 5 mg |
| Maize Starch | 20 mg |
| Microcrystalline Cellulose | 15 mg |
| Magnesium Stearate | 2 mg |

Granulated with Polyvinylpyrrolidone 10% w/v in 50% w/v aqueous ethanol. The tetrazole, salbutamol, Maize starch and Microcrystalline Cellulose were mixed together, and granulated with the alcoholic Polyvinylpyrrolidone. The resulting granules were dried, and compressed to produce tablets, each tablet having a weight of approximately 142 mg.

Example 2

| Capsule | |
| --- | --- |
| 3-(5-Tetrazolyl)thioxanthone-10,10-dioxoide | 100 mg |
| Salbutamol | 10 mg |
| Lactose | 100 mg |
| Maize Starch | 100 mg |
| Magnesium Stearate | 10 mg |

The ingredients were mixed together until homogeneous and 320 mg of the resulting mixture filled into each hard gellatin capsule.

EXAMPLE 3

A tablet and capsule were formulated as described in Examples 1 and 2, using 2-(5-tetrazolyl)phenoxathiin-10,10-dioxide in place of 3-(5-tetrazolyl)thioxanthone-10,10-dioxide.

Example 4

| Capsule | |
| --- | --- |
| 3-Carboxythioxanthone-10,10-dioxide | 200 mg |
| Salbutamol | 20 mg |
| Lactose | 200 mg |
| Maize Starch | 200 mg |
| Magnesium Stearate | 20 mg |

The ingredients were admixed as described in Example 2 and 630 mg of the resulting mixture filled into each hard gellatin capsule.

EXAMPLE 5

Interaction between 3-(5-tetrazolyl)thioxanthone-10,10-dioixde (compound of formula (II)) and Salbutamol The experimental procedure used was that using chopped human lung tissue substantially as described in Br. Med. J. 3, 272 (1968).

| Concentration of Compound (II) | Percentage Inhibition of Histemine Release | | | |
| --- | --- | --- | --- | --- |
| | None | Salbutamol Concentration | | |
| | | $10^{-10}M$ | $10^{-9}M$ | $10^{-8}M$ |
| A. None | — | 17 | 0 | |
| $10^{-8}M$ | 15 | 58 | 49 | |
| B. None | — | 0.9 | 22 | 27 |
| $10^{-7}M$ | −13 | −5 | 80.5 | 64 |
| $10^{-8}M$ | −14.5 | −11 | 96 | 38 |

What we claim is:

1. A synergistic pharmaceutical composition for use as an anti-allergic comprising a compound of formula (I)

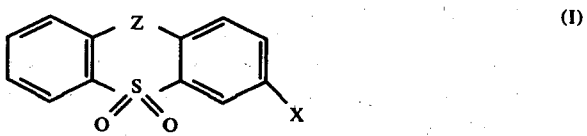

wherein Z is oxygen or carbonyl and Z is carboxyl or 5-tetrazolyl or a pharmaceutically acceptable salt thereof, with a stimulant selected from salbutamol, terbutaline, fenoterol, trimetoquinol and carbuterol, or a pharmaceutically acceptable salt thereof, wherein the ratio by weight of the compound formula (I) or a pharmaceutically acceptable salt thereof to stimulant or a pharmaceutically acceptable salt thereof is in the range of 1:1 to 200:1.

2. A composition as claimed in claim 1 wherein the compound of formula (I) is selected from:
  3-(5-tetrazolyl)thioxanthone-10,10-dioxide;
  2-(5-tetrazolyl)phenoxathiin-10,10-dioxide;
  3-carboxylthioxanthone-10,10-dioxide;
  and pharmaceutically acceptable salts thereof.

3. The composition of claim 1 wherein the stimulant is salbutamol.

4. A composition as claimed in claim 1 comprising from 1 to 400mg of a compound of formula (I) or a pharmaceutically acceptable salt thereof.

5. A composition as claimed in claim 1 comprising from 1 to 200 mg. of a compound of formula (I) or a pharmaceutically acceptable salt thereof.

6. A composition as claimed in claim 4 comprising from 5 to 100% by weight of the effective bronchodilating dose of the stimulant or a pharmaceutically acceptable salt thereof.

7. A composition as claimed in claim 3 comprising from 1 to 20 mg. of salbutamol or a pharmaceutically acceptable salt thereof.

8. A composition as claimed in claim 1 in the form of a discrete unit suitable for oral administration.

9. A composition as claimed in claim 1 in the form of a tablet, capsule or cachet.

10. A composition as claimed in claim 1 in the form of a solution or suspension in a liquid medium.

11. A method for the treatment or prophylaxis of a mammal susceptible to an allergic condition by administering to said mammal, sequentially or simultaneously, a non-toxic effective anti-allergic amount of a composition as claimed in claim 1.

12. A method as claimed in claim 11 for the treatment or prophylaxis of asthma, allergic rhinitis, conjunctivitis, urticaria or eczema.

13. A method as claimed in claim 11 for the treatment or prophylaxis of 'intrinsic' asthma or 'extrinsic' asthma.

* * * * *